United States Patent
Kessler et al.

(10) Patent No.: US 7,395,713 B2
(45) Date of Patent: *Jul. 8, 2008

(54) TRAY-FED SCANNING MICROSCOPE SYSTEM AND METHOD PRIMARILY FOR IMMOBILIZING PARTS DURING INSPECTION

(75) Inventors: Lawrence Kessler, Buffalo Grove, IL (US); John Billone, Des Plaines, IL (US)

(73) Assignee: Sonoscan, Inc., Elk Grove Villiage, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/090,962

(22) Filed: Mar. 25, 2005

(65) Prior Publication Data

US 2006/0081051 A1    Apr. 20, 2006

Related U.S. Application Data

(63) Continuation of application No. 10/821,481, filed on Apr. 9, 2004, now Pat. No. 6,912,908.

(51) Int. Cl.
*G01N 29/26* (2006.01)
(52) U.S. Cl. .......................................... 73/620; 73/644
(58) Field of Classification Search .................. 73/818, 73/620, 644, 606, 618
See application file for complete search history.

(56) References Cited

U.S. PATENT DOCUMENTS

| | | | |
|---|---|---|---|
| 3,737,573 A | 6/1973 | Kessler | |
| 3,790,281 A | 2/1974 | Kessler et al. | |
| 3,850,027 A | 11/1974 | Nakaniishi et al. | |
| 3,886,793 A | 6/1975 | Cramer et al. | |
| 3,898,839 A | 8/1975 | White | |
| 4,008,602 A | 2/1977 | Love | |
| 4,012,951 A | 3/1977 | Kessler | |
| 4,208,915 A | 6/1980 | Edwards | |
| 4,332,016 A | 5/1982 | Bernsten | |
| 4,518,992 A | 5/1985 | Kessler et al. | |
| 4,563,900 A | 1/1986 | Harada et al. | |
| 5,077,695 A | 12/1991 | Khuri-Yakub et al. | |
| 5,431,054 A | 7/1995 | Reeves et al. | |
| 5,600,068 A | 2/1997 | Kessler et al. | |
| 5,684,252 A | 11/1997 | Kessler et al. | |
| 6,460,414 B1 | 10/2002 | Erickson et al. | |
| 7,181,969 B2 * | 2/2007 | Busch et al. | 73/618 |

OTHER PUBLICATIONS

PCT Written Opinion, International Application No. PCT/US04/10911, dated Feb. 16, 2005 (5 pages).
PCT International Search Report, PCT/US04/10911, dated Feb. 16, 2005 (2 pages).

* cited by examiner

*Primary Examiner*—John E Chapman
(74) *Attorney, Agent, or Firm*—Welsh & Katz, Ltd.

(57) ABSTRACT

An improved scanning station and method for a tray-fed scanning acoustic microscope has a vacuum system which at least assists in immobilizing loosely held parts in the trays during insonification by an ultrasonic beam generator.

20 Claims, 8 Drawing Sheets

TRAY-FED SCANNING MICROSCOPE SYSTEM AND METHOD PRIMARILY FOR IMMOBILIZING PARTS DURING INSPECTION

BACKGROUND OF THE INVENTION

This invention relates to scanning acoustic microscopes used in the non-destructive testing of microcircuit parts, and is addressed primarily to a system and method for enhancing the capability of such systems to immobilize the parts under test.

A scanning acoustic microscope typically has an ultrasonic beam generator that is traversed rapidly back and forth over a part under test. To traverse the entire part, either the beam generator is scanned in two dimensions, or in one dimension, as the part is translated through the beam in the orthogonal dimension.

The image output of the scanning acoustic microscope is employed for the non-destructive analysis of the internal physical characteristics of the part. The scanning acoustic microscope is able to penetrate through the part surface and image microscopic internal features in solids such as metals, ceramics, polymers, and composites. Typical components tested include microelectronic components such as integrated circuits (IC's), multi-layer ceramic capacitors, and multi-chip modules. Faults typical of the parts tested include delaminations, cracks, tilts of discrete layers, disbonds, underfill coverage, and voiding.

Such components may be carried to the scanning station in trays known in the art as "JEDEC" trays. JEDEC trays are characterized by comprising an X-Y matrix of individual cells or pockets custom shaped and sized for the particular parts being carried.

It is a characteristic of high-frequency ultrasound that, while able to penetrate solids such as those described, high frequency ultrasound beams cannot pass through an air gap between the ultrasound beam generator and the part under test without severe attenuation. A fluid medium is therefore used to couple the high-frequency output of the scanning head of the ultrasonic beam generator to the part. The fluid medium is usually water, although alcohol and other fluids may be used. In one common approach, a coupling fluid is dispensed in a falling stream or an upwardly ejected fountain which surrounds the ultrasonic beam.

It is the inevitable design trend in microelectronics that parts such as IC's are becoming ever smaller. And as they diminish in size, the parts become more difficult to handle and manipulate, especially when tested in a production environment. In particular, a coupling fluid stream is very apt to agitate and even dislodge such small parts from the trays as they move through the scanning acoustic microscope.

It is important to understand that JEDEC trays were developed as a means to carry integrated circuits and other semiconductor products from one semiconductor fabrication step or station to another. As the individual parts may be removed from and placed in their individual pockets a number of times during the fabrication process, typically by vacuum "pickers", they must be loosely held in their pockets so that they may be easily removed and replaced without damage to the parts.

JEDEC trays were not designed to hold parts during inspection by a scanning ultrasonic microscope which requires that the parts be completely immobilized during inspection. The loose fit of part to pocket facilitates the basic transport function of JEDEC trays, but creates significant problems when trays of parts are inspected by a scanning ultrasonic microscope. One major problem is the dislodgement of parts, particular small parts, from the trays. A second significant problem is to immobilize the parts as they are being ultrasonically scanned.

If the parts are not immobilized during the insonification operation, the coupling fluid stream agitates the parts, causing them to move in their respective pockets as they are being interrogated by the scanned ultrasound beam. Movement of the parts during inspection distorts the inspection signals developed, producing errors which may be serious enough to vitiate the entire inspection process. For example, if the inspection process is intended to identify very fine cracks in a semiconductor die, the signal distortions introduced by part movement during ultrasonic interrogation may introduce errors of such magnitude that such cracks cannot be reliably detected.

Another problem with scanning JEDEC trays of parts is that the typically plastic trays may be warped as a result of defective manufacture or prolonged use or abuse. A warped tray changes the relative elevation and planarity of the parts in the two-dimensional array of parts which may result in inspection errors.

U.S. Pat. No. 5,684,252 to Kessler et al., of common ownership herewith, addresses the dislodgement and immobilization problems, disclosing and claiming a tray-fed scanning acoustic microscope system in which trays of parts are each paired with an open mesh screen to hold the parts in the trays as they pass through the scanning station. The screens are removed from the trays after the scanning operation has been completed. This technique requires a large number of screens of various sizes and configurations to accommodate different tray sizes and configurations. The screens represent an added capital and maintenance expense, and their handling generates a labor cost and delay.

U.S. Pat. No. 6,357,136, also issued to the owner of the present application, teaches a solution to the problem of dislodged parts, and in some applications of part immobilization, by providing a single stationary hold-down structure between the ultrasound beam generator and the part-holding trays. The cost of multiple screens is overcome by the use of a single hold-down structure which prevents the coupling fluid from dislodging parts from their trays during the inspection process.

The system and method of the U.S. Pat. No. 6,357,136 functions best when used with JEDEC or other trays of parts in which height (thickness) of the individual parts (typically identical) being tested is greater than the depth of the pocket which holds the part. The stationary hold-down structure is thus able to physically engage the protruding parts and firmly immobilize them in their respective pockets during interrogation by the ultrasonic beam.

However, in applications in which the height of the inspected parts is less than the containing pocket depth, the stationary hold-down structure, while still effective to prevent part dislodgement, is not as effective in immobilizing the contained parts during inspection. To combat the inspection accuracy problem, it is necessary in certain applications to slow the scanning rate, however this reduces the inspection throughput rate.

OBJECTS OF THE INVENTION

It is a general object of the invention to provide solutions to certain problems incurred in tray-fed inspection of parts in a scanning acoustic microscope.

It is an object to enhance the capability of a tray-fed scanning acoustic microscope to immobilize microelectronic ICs

DESCRIPTION OF THE FIGURES

FIG. 2A is a perspective view of the structure, while FIGS. 2B and 2C show side and end views of the structure, respectively.

FIG. 3 is a cross-sectional view of the stationary parts-hold-down structure according to an aspect of the invention.

DESCRIPTION OF THE PREFERRED EMBODIMENT

The present invention is directed to a scanning acoustic microscope inspection system and method that enables the inspection of parts, especially parts of such small size to be incapable of being handled by prior art tray-fed scanning acoustic microscope systems.

An execution of the invention is illustrated in the figures, in which like reference numerals in different figures indicate like structure. The elements of the depicted execution will be first listed and identified with brief descriptive annotations where necessary to enlighten one skilled in the art, followed by a concise description of the structural details and operational method of the system.

Structure of the Preferred Embodiment

| Reference Numeral | Description |
|---|---|
| 20 | tray-fed scanning acoustic microscope |
| 21A | station for loading trays of parts |
| 21B | tray-scanning station |
| 21C | drying station for drying trays of parts |
| 22 | tray for conveying the parts |
| 23 | surface of tray 22 |
| 24 | opening in pocket 24A |
| 24A | pocket for receiving a part 25 |
| 24B | bottom or ledge of pocket 24A |
| 25 | a microelectronic part |
| 25A | a part dislodged from its pocket |
| 26 | conveyor - may be two belts engaging opposite sides of the trays |
| 28 | direction of movement of conveyor 26 and trays 22 |
| 30 | ultrasonic beam generator |
| 32 | ultrasonic beam |
| 36 | a parts-hold-down structure |
| 37 | transducer head |
| 38 | collar for dispensing coupling fluid |
| 40 | coupling fluid |
| 42 | catch tank |
| 50 | slot |
| 56 | a side of the structure |
| 58 | bottom pan |
| 60 | cant |
| 64 | holes for receiving hold-down screws |
| 70 | parts hold-down device |
| 72 | frame |
| 74A, 74B | mesh |
| 78 | flange |
| 84A | air knife |
| 84B | air knife |
| 86 | streams of air |
| 90A | plane of air knife 84A |
| 91 | vacuum dryer |
| 91A, 91B | open sides of structure 36 |
| 92 | slots |
| 94 | transducer head |
| 95 | ultrasonic beam |
| 96 | pool of coupling fluid |
| 98 | structure |
| 100 | brush |
| 102 | squeegee |
| 104 | stream of air |
| 106 | air nozzle |
| 110 | vacuum system |
| 112 | pump |
| 113 | top wall of plenum chamber 114 |
| 114 | plenum chamber |
| 115 | openings |
| 116 | suction line |
| 117 | pump reservoir |
| 118 | recirculation line |
| 119 | main reservoir |
| 120 | perforate top wall |
| 121 | filter in drain of catch tank 42 |
| 122 | filter |
| 124 | fluid pump for recirculating coupling fluid |
| 126 | X motion stage |
| 128 | X-Y motion stage |
| 130 | vacuum system |
| 132 | plenum chamber |
| 133 | top wall |
| 134 | openings |
| 136 | drying station |
| 137 | top wall |
| 138 | dryer plenum chamber |
| 139 | slots |
| 140 | allocator valve |
| 141 | line |
| 142 | end apertures |
| 143 | control means |
| 144 | additional row of openings |

-continued

| Reference Numeral | Description |
| --- | --- |
| 148 | plenum chamber |
| 150 | motion stage |
| 152 | connecting member |
| 154 | connecting member |
| 156 | pattern of openings |
| 160 | suction elements |
| 162 | pump |
| 164 | distribution system |
| 166 | suction commutator |
| 168 | control means |
| 170 | motion stage |

Figure 1:
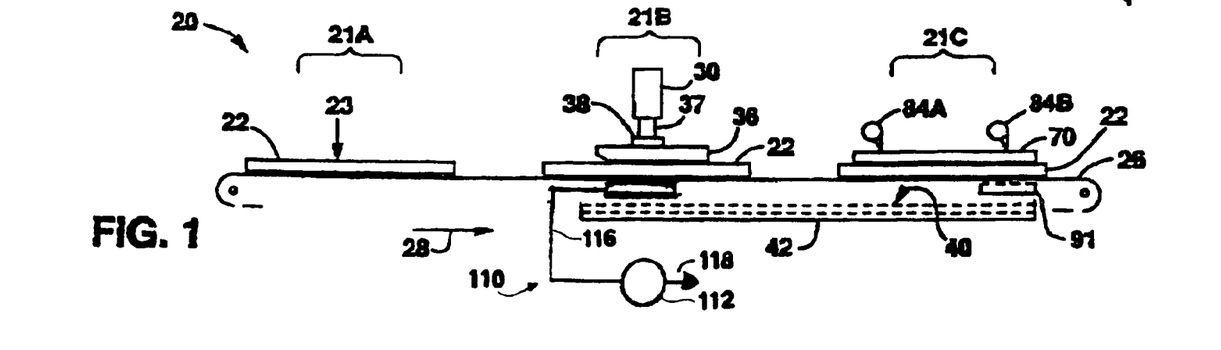
FIG. 1 is a schematic view in elevation of a multi-stage tray-fed scanning acoustic microscope apparatus embodying the invention.

A scanning acoustic microscope 20 shown in FIG. 1 comprises a station 21A for loading trays of parts (one tray 22 is shown), an improved tray-scanning station 21B for handling trays of loosely held parts, and a drying station 21C for drying trays of parts. A tray 22 holds parts as they are conveyed successively to the tray-scanning station 21B and to the drying station 21C. The tray 22 may be of any of a variety of types and constructions such as a JEDEC tray—a standard in the industry, of which there are more than a hundred different configurations. As an example, the tray 22 used for exemplary purposes has a width dimension of 5.25 in.

and a length dimension of 12.5 in.

Figure 1A:
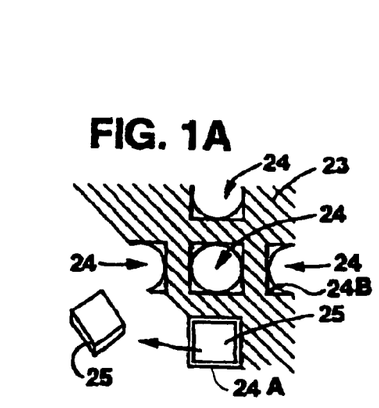
FIG. 1A is a detail view of the surface of a parts-holding tray passing through the apparatus of FIG. 1.

With reference to FIG. 1A, surface 23 of tray 22 is shown as having of a plurality of cells or pockets 24A for receiving ICs or other small parts, one of which is indicated at 25. In the JEDEC tray used as an example, there are 12 pockets widthwise and 29 pockets length-wise, for a total of 348 pockets. Each pocket 24A has the capacity for loosely holding a single microelectronic part that may be, by way of example, 0.22 in. square and 0.125 in. thick. The ledge or bottom 24B of each of the pockets 24A has an opening 24 to allow a flow of coupling fluid around the loosely held parts and through the pockets 24A. Other JEDEC trays have a pocket configuration which lacks a bottom; the parts are supported in their respective pockets by simple ties across the opening. This style of pocket promotes a greater flow of coupling fluid around the parts than the illustrated pocket 24A wherein the parts sit on a ledge or bottom 24B which tends to partially impede the flow of coupling fluid around the part 25 during insonification.

A conveyor 26, which may comprise a pair of Neoprene™ belts on opposite sides of the trays, moves tray 22 to tray-scanning station 21B, then to drying station 21C. Tray-scanning station 21B has an ultrasonic beam generator 30 that emits an ultrasonic beam 32 (shown in FIG. 3) focused on the parts 25 carried by tray 22 as the tray 22 passes in the direction indicated by arrow 28. Ultrasonic beam generator 30 has a transducer head 37 for projecting an ultrasonic beam 32. The transducer head 37 also has a collar 38 for dispensing coaxially with beam 32 a coupling fluid 40 such as water. Ultrasonic beam generator 30 is moved rapidly transversely (the "X" axis in this application) back and forth across the trays as the trays are moved longitudinally by the conveyor 26. The motion stage for driving ultrasonic beam generator back and forth (not shown in this view) may be that described and claimed in U.S. Pat. No. 4,781,067 to Frank J. Cichanski, of common ownership herewith.

A stationary parts-hold-down structure 36 is situated between the ultrasonic beam generator 30 and the trays 22 being conveyed through station 21B, and closely contiguous to the trays 22.

A means for capturing the coupling fluid 40 that drains through parts-hold-down structure 36 is shown as a coupling fluid catch tank 42 located beneath scanning station 21B and drying station 21C.

The coupling fluid 40 dispensed from the collar 38 undesirably tends to dislodge parts 25 from the trays 22 and to agitate them even if not dislodged. By way of example, FIG. 1A shows (exaggerated) that part 25 does not fit snugly in pocket 24A and is likely to vibrate or move around in the pocket when impinged by a stream of falling coupling fluid.

However, any movement of a scanned part while being interrogated by the ultrasound beam may cause signal distortion and errors sufficiently great to render the inspection operation ineffective. One objective of this invention is to at least assist in securing and immobilizing the parts 25 in their respective pockets 24A to reduce inspection errors associated with movement of the scanned parts during the inspection operation.

Parts-hold-down structure 36 has at least one opening therein which is sized and positioned to pass a scanned ultrasound beam 32 from ultrasonic beam generator 30, but not to pass small parts 25 from the trays 22. The opening is indicated as being a slot 50 in this embodiment of the invention. The ultrasonic beam generator 30 is translated transverse to the path of tray 22 (the "X" axis in this application), and the opening 50 is of sufficient width in the direction of tray movement to pass the coupling fluid 40 and the transversely moved ultrasound beam 32, but not to pass the small parts in the trays.

While stationary during operation, the structure 36 may be adjusted vertically between runs by means of an elevator structure (not shown) in order to accommodate trays of different heights. The elevator structure may be of conventional construction.

Figure 2:
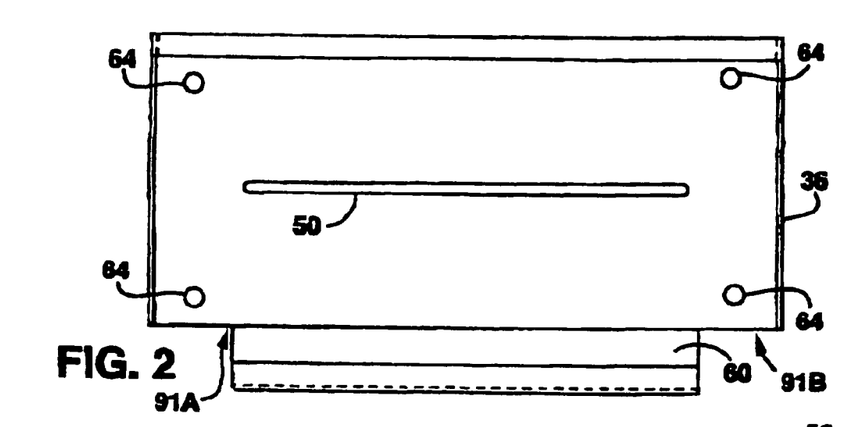
FIG. 2 is a plan view of a stationary parts-hold-down structure according to an aspect of the invention.
Figures 2A, 2B, 3:
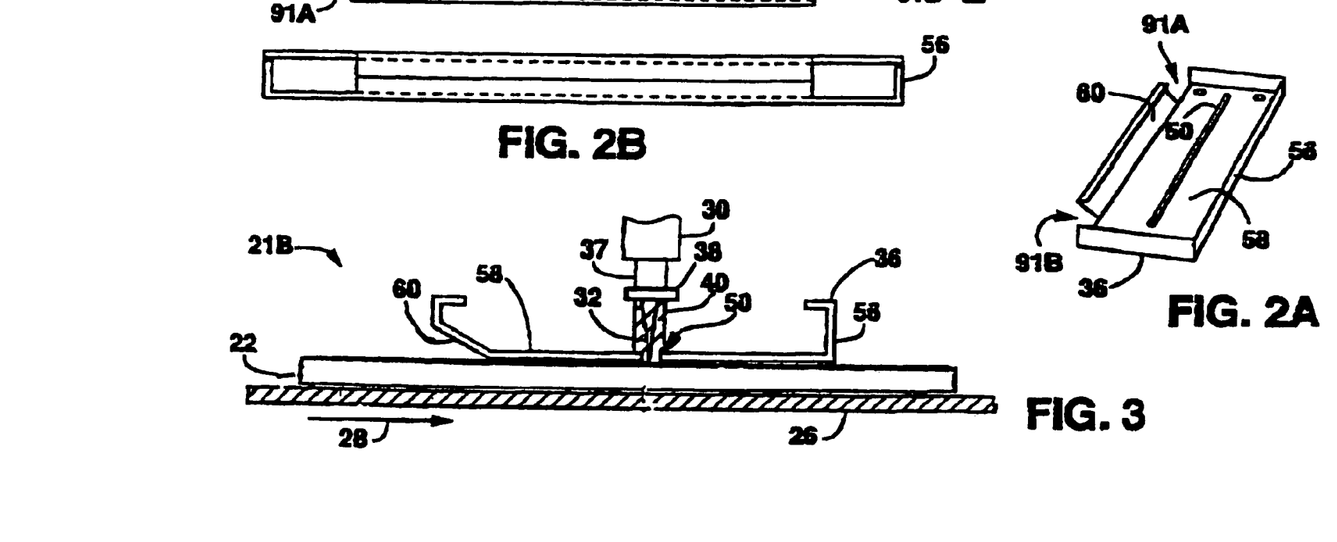

The ultrasonic beam generator 30 is depicted in FIG. 3 as focusing an ultrasound beam 32 through slot 50, where it impinges on a succession of parts 25 in tray 22 in the tray's traverse through the transverse to slot 50.

An attribute of the parts-hold-down structure 36 is that trays 22 of small parts 25 may be inspected without the parts being dislodged from the trays by coupling fluid as they traverse scanning station 21B. In trays of the type wherein the parts protrude above the upper surface of the tray, the hold-down structure 36 serves to physically press the parts down into the pockets and immobilize them during inspection. However, in the illustrated application the height (thickness) of the parts 25 is less than the depth of the pockets 24A. The parts 25 are therefore not physically held down in the pockets during inspection and, absent the present teachings, are likely to be agitated by the impinging stream of coupling fluid during inspection. This subject will be treated at length below.

Figure 2C:
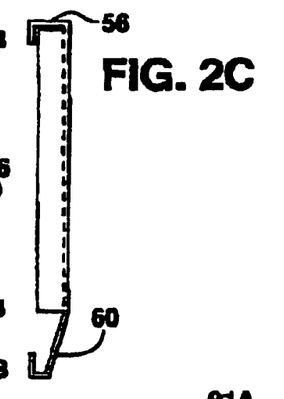

With reference to FIGS. 2-2C, the parts-hold-down structure 36 is depicted as having three closed sides, one of which is indicated at 56. Structure 36 has a bottom pan 58 that is slanted upwardly in the direction of approach of the conveyed trays 22 to form a fourth side having an upward cant 60. The purpose of the upward cant 60 is to engage and re-nest dislodged parts. The upward cant 60 relative to bottom pan 58 may be an acute angle in the range of 10 to 30 degrees, and is preferably about 10 degrees.

By way of example, the parts-hold-down structure 36 may have a length of about 8.25 in. and a width of about 3.75 in., with the upward cant section extending outwardly from the bottom pan 58 by about 0.69 in. The depth of the shallow sides may be about 0.44 in. The length of the slot may be about 5.75 in, and its width about 0.093 in., all by way of example. Structure 36 may be composed of 0.032 stainless steel shim stock. It is noted that the bottom surface 58 of pan 60 must be unaffected by the machining of the slot and remain flat within about 0.01 in. to ensure the close contiguity of structure 36 and the tray 22 with its parts 25 passing beneath.

Structure 36 is held stationary by four machine screws (not shown), preferably of stainless steel. The four screws and inserted through the four holes 64, and threaded into a fixed part of the scanning acoustic microscope.

Figure 13:
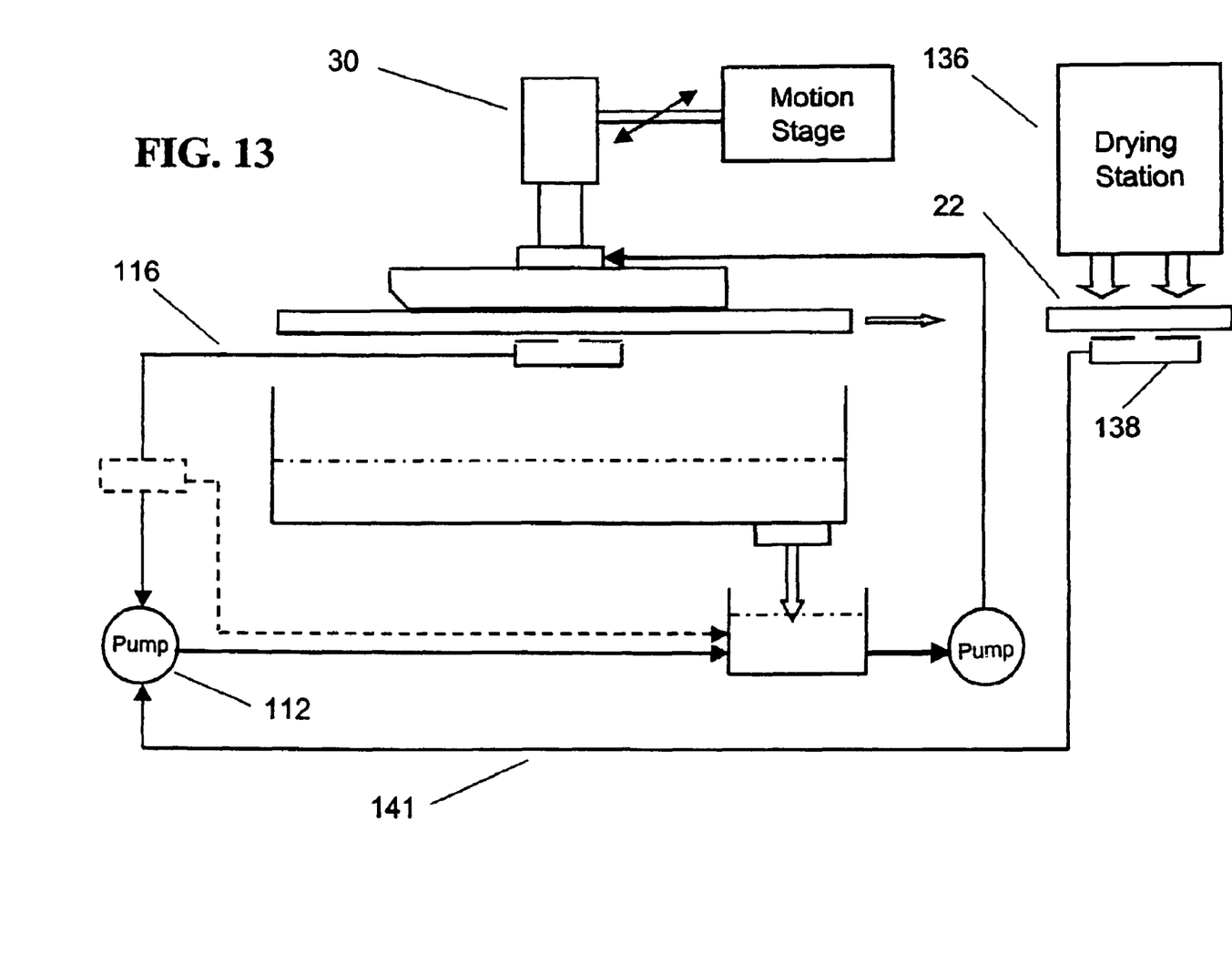
FIGS. 13-15 illustrate a vacuum system in which a dryer station and a hold-down vacuum system employ a common vacuum pump.

With reference to FIGS. 1 and 13, drying station 21C provides for drying trays of parts that have been insonified through a coupling fluid. Essentially, the drying station 21C comprises a dryer for removing coupling fluid, here shown as means for directing a stream or streams of forced gas onto wet trays of parts passing through the drying station.

Figures 1B, 1C:
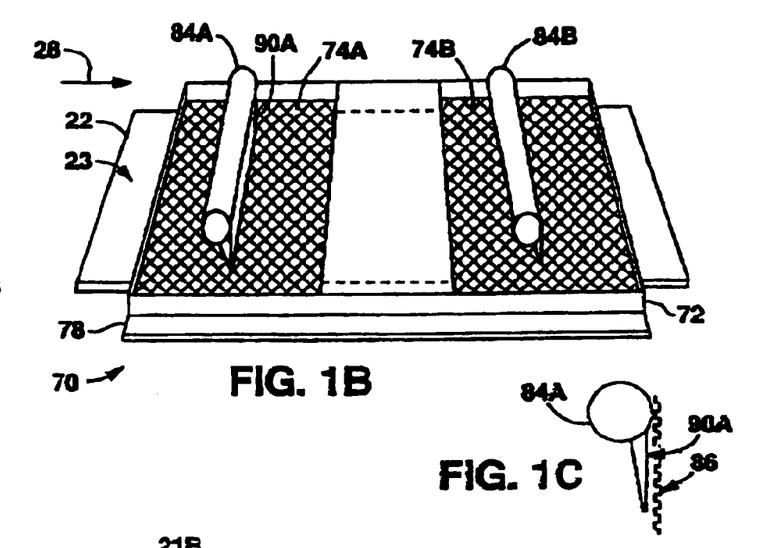
FIG. 1B is a perspective view of a stationary parts-hold-down device used in a drying station.
FIG. 1C depicts operating details of a dryer element shown by FIG. 1B.

However, the dryer undesirably agitates the parts and tends to dislodge them from the trays. A stationary parts hold-down device 70 is situated between the dryer and the trays and is positioned closely contiguous to the trays. The stationary hold-down device 70 is shown in this embodiment of the invention as comprising a frame 72 having a pattern of openings sized and positioned to pass streams of forced gas to the trays while precluding the small parts from escaping from the trays. The pattern of openings is indicated in this embodiment as comprising a two-section mesh 74A and 74B. The parts-hold-device 70 is made stationary by means of a flange 78 attached to a fixed part of the scanning acoustic microscope. An identical flange (not shown) is located on the opposite side of the frame 72.

While stationary during operation, like the structure 36 the hold-down device 70 may be adjusted vertically between runs by means of an elevator structure (not shown) in order to accommodate trays of different heights. The elevator structure may be of conventional construction.

Frame 72 is indicated as straddling a tray 22 of small, loosely held parts moving in the direction indicated by arrow 28. The parts placement on the surface 23 of tray 22 is depicted by FIG. 1A. The dryer in this embodiment is shown as comprising a pair of air knives 84A and 84B, indicated as being identical in construction. As depicted in FIG. 1C, air knife 84A develops a stream of air 86, depicted by the dash lines, along a plane 90A, producing a knife-like stream of air directed downwardly, in this example, toward the wet parts. Air knife 84B develops a similar stream of air.

As will be described in more detail below, moisture removal from the parts and trays may be enhanced by the provision of a vacuum dryer, shown schematically in FIG. 1 at 91.

The coupling fluid 40 that empties through slot 50 in structure 36, and the fluid that flows from the open sides 91A and 91B of the structure 36 (see FIG. 2A), as well as the coupling fluid 40 blown from parts 25 by the stream of forced gas from the air knives 84A and 84B of FIG. 1B, drains down through the tray 22 and the conveyor 26, and into the coupling fluid reservoir 42. From there, the coupling fluid may be filtered and recirculated to the fluid-dispensing collar 38 of the ultrasound beam generator 30.

Figures 4, 5, 6:
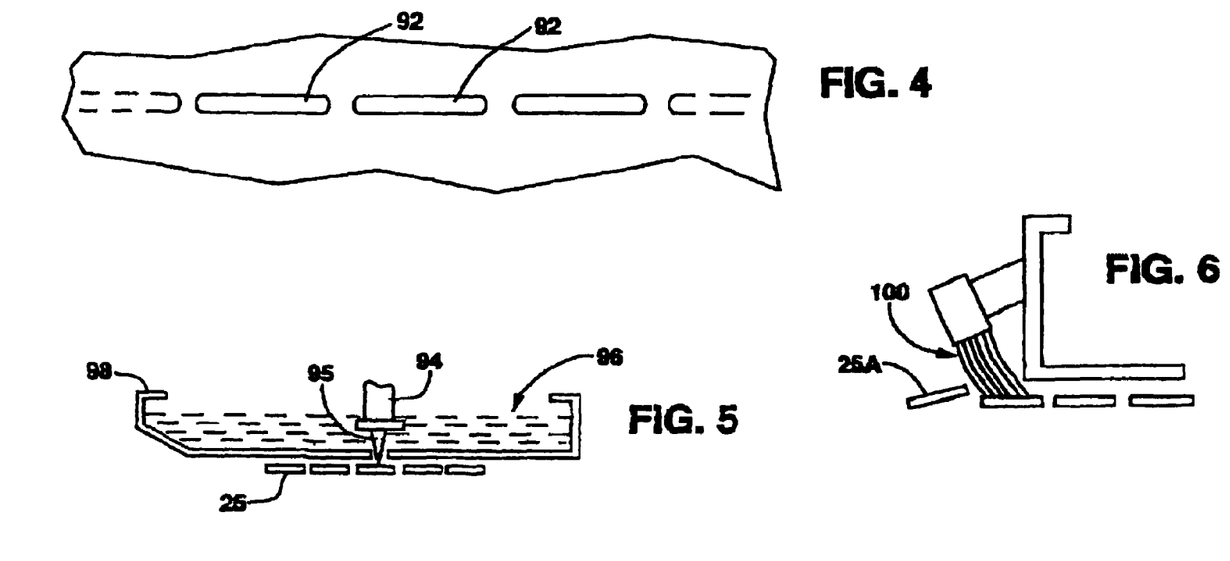
FIG. 4 is a view of a section of a structure according to an aspect of the invention, and depicting an alternate embodiment of a beam-passing slot.
FIG. 5 is a cross-sectional view of the structure showing an alternate embodiment of the structure depicted in FIG. 3.
FIGS. 6-8 depict alternate means for re-nesting partially dislodged parts in trays before they pass through the scanning station.

Whereas a continuous uninterrupted slot 50 in structure 36 has been shown and described, the opening in structure 36 may take the form of a series of slots 92, as shown in FIG. 4. The slots 92 are sized and spaced to align with the parts passing beneath in such a way as to expose to the acoustic probe the parts, or specific areas of the parts, which are to be inspected.

With reference to FIG. 5, in ultra-high-resolution applications wherein the focal length of the beam is short, the transducer head 94 emitting an ultrasonic beam 95 may be submerged in the pool 96 of coupling fluid collected in the structure 98. An additional source of coupling fluid is metered into the structure 98 to control the desired depth of fluid.

Figure 7:
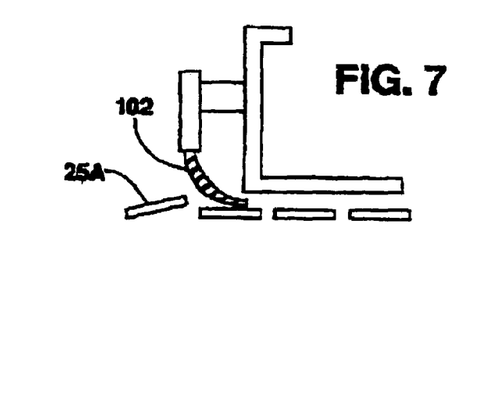
Figure 8:
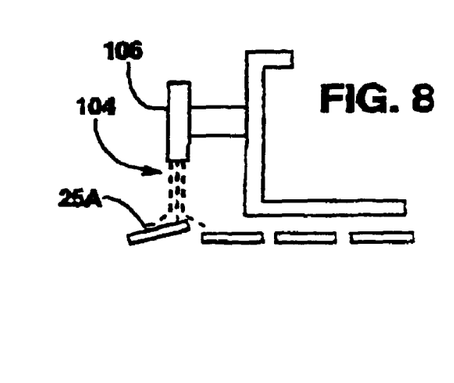

Whereas the re-nesting of a dislodged part 25A is accomplished in the described embodiment by means of cant 60, re-nesting can be accomplished in other ways, such as by means of a soft brush 100 (FIG. 6), a squeegee 102 (FIG. 7), or a gentle air stream 104 produced by an air nozzle 106 (FIG. 8).

In the drying station, coupling fluid removal is accomplished in the preferred execution by means of a pair of gas jets. A single jet may be employed instead. The gas may be heated. The jet or jets may be pulsed or have their gas volume delivered according to a prescribed rate variation program. As will be described in more detail hereinafter, in addition to gas jets or in lieu of gas jets, or in combination with gas jets, the trays may have suction applied.

In accordance with an aspect of the present invention an improved tray-fed scanning acoustic microscope is provided for inspecting perforate trays of loosely held parts. The microscope includes a tray conveyor, a coupling fluid dispenser, and ultrasonic beam generator configured to direct an ultrasonic beam through the coupling fluid onto the trays during scanning of the trays. To mitigate the afore-described tendency of the dispensed coupling fluid to undesirably agitate the parts during scanning, there is provided a vacuum system configured to draw a vacuum on the bottom of the trays to at least assist in securing and immobilizing the parts in the trays during tray scanning. As will be explained, the vacuum system draws air into the trays and out through openings in a bottom of each tray. The air flow created entrains coupling fluid, and the pressure applied by these fluids as they flow around the parts firmly holds them firmly in their respective pockets during scanning of the trays.

Figures 9, 10:
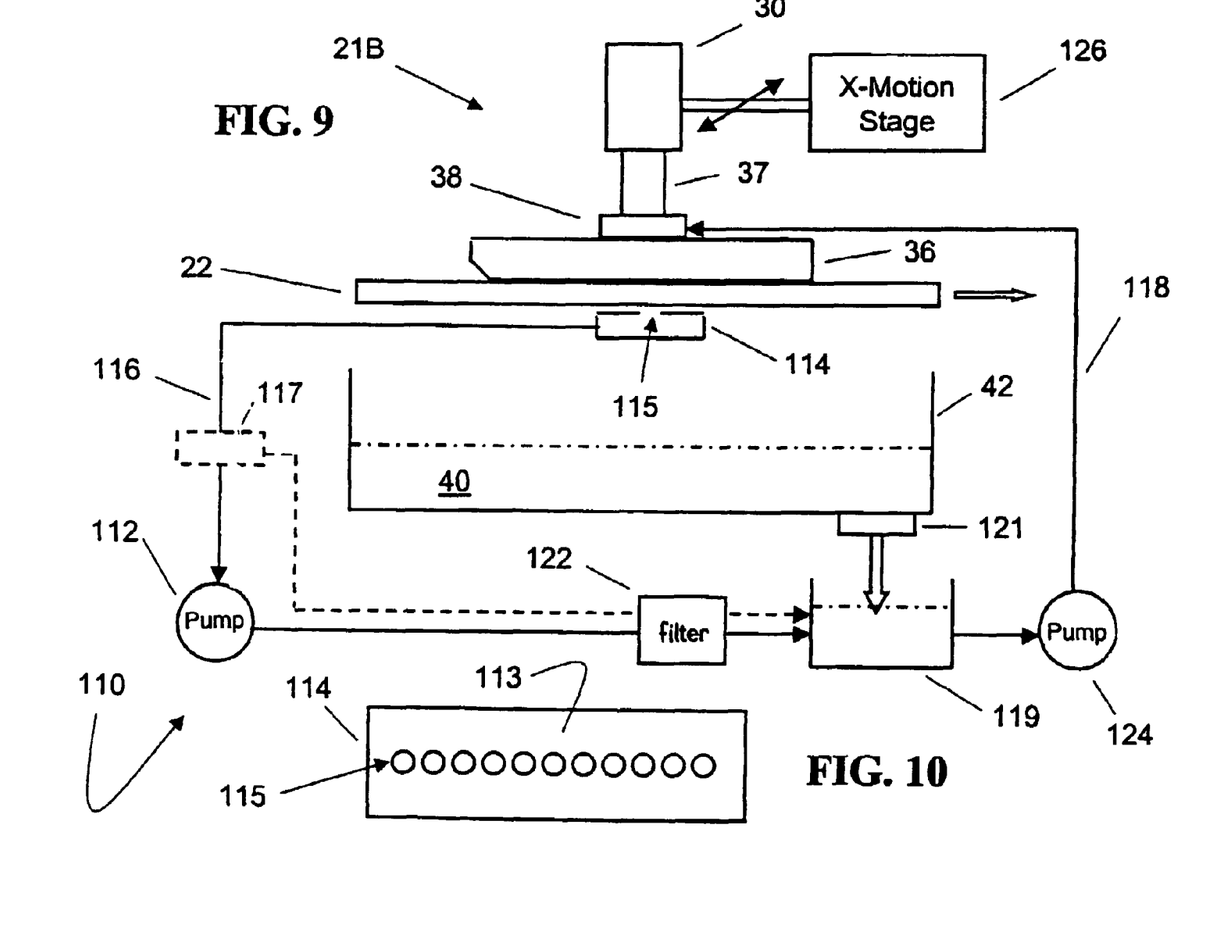
FIG. 9 depicts a vacuum system implementing an aspect of the invention.
FIG. 10 is a top view of a plenum chamber constituting part of the FIG. 9 vacuum system.

As shown in FIG. 9, a variant of the system depicted in FIG. 1, the vacuum system 110 comprises a vacuum pump 112 coupled through a suction line 116 to a plenum chamber 114. As described above with respect to FIG. 1A, the trays 22 are perforated by a series of openings 24, one in each pocket 24A. The plenum chamber 114 has a perforate top wall 113 perforated with a series of opening 115 shown more clearly in plan view in FIG. 10. Vacuum created by the pump 112 draws a stream of air through the openings 24 in the tray 22 and through the openings 115 in the top wall 113 of the vacuum chamber 114. The pressure applied by the air flow and entrained coupling fluid 40 is effective to immobilize the parts 25 in their respective pockets 24A during the scanning operation. The coupling fluid passed by pump 112 is fed to a main reservoir 119 used to store coupling fluid drained from the catch tank 42. A filter 121 at the drain of the catch tank 42 removes impurities from the coupling fluid collected in the catch tank 42. For simplicity of illustration, the conveyer 26 is not shown in FIG. 9 or succeeding figures.

The pump 112 may be of the single or double diaphragm type, or any of a number of other suitable types that are adapted to create a suitable vacuum without being adversely affected by the entrained coupling fluid. If the pump 112 is of the type requiring a fluid separation reservoir, as shown in dotted lines at 117 the effluent from the reservoir 117 may be fed directly to the main reservoir 119 (optional pump not shown).

To reduce the need to replenish coupling fluid, the coupling fluid in the main reservoir 119 is recirculated by a fluid pump 124 through line 118 back to the coupling fluid dispensing collar 38. A filter 122 in the suction line 116 removes contaminants that might interfere with the inspection process.

The FIG. 9 embodiment is illustrated as being adapted to have the ultrasonic beam generator 30 reciprocated transversely across the trays 22 by an X-motion stage 126. It will be understood that as the beam generator 30 is scanned (in and out of the paper in FIG. 9), to optimize the effect of the vacuum system 110 the beam is aligned with the series of vacuum opening 115 in the top wall 120 of the plenum chamber 114. As in the FIG. 1 embodiment, in FIG. 9 X-Y scanning of the trays is achieved by causing the trays 22 to be conveyed in the direction of the arrow (the "Y" axis in this application) as the beam generator is being scanned along the orthogonal X axis by the X-motion stage 126.

Figure 11:
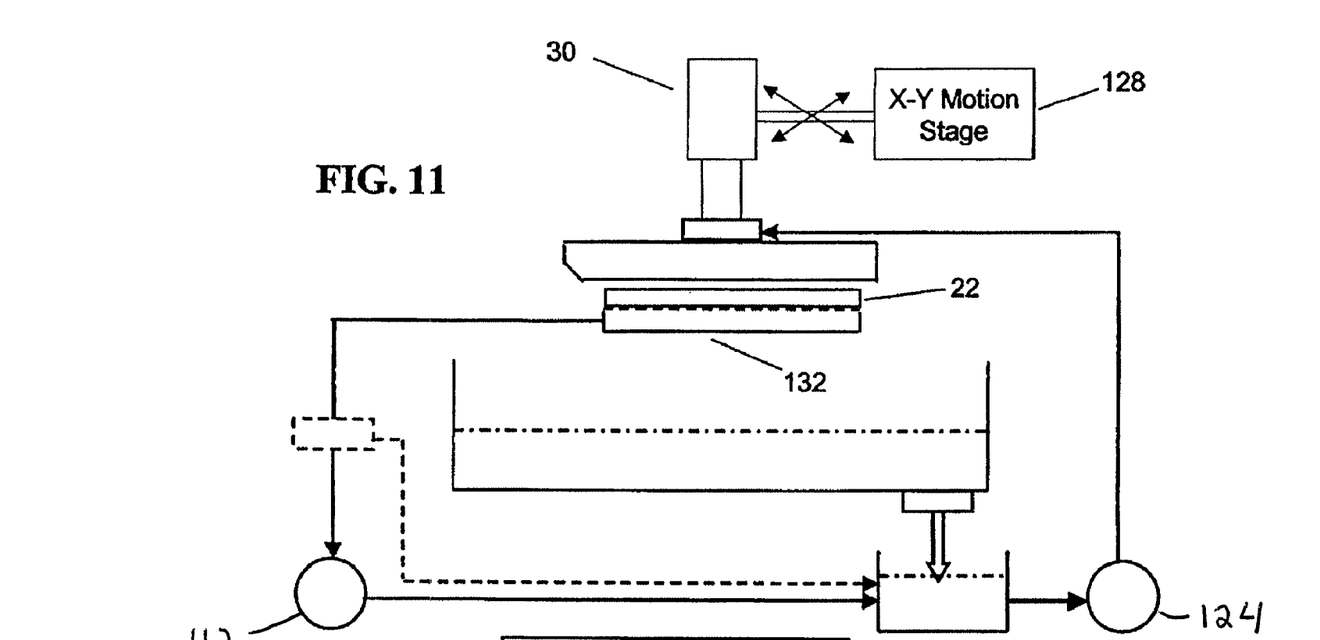
FIG. 11 illustrates a vacuum system similar to the FIG. 10 system but configured for an acoustic microscope scanned in an X-Y format.
Figure 12:
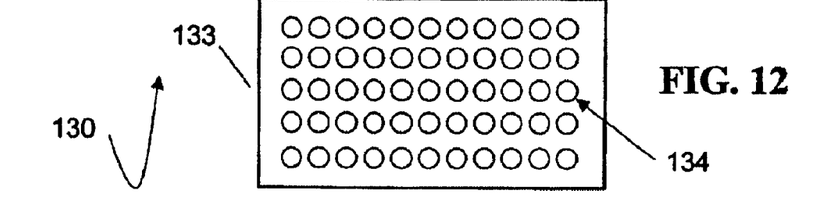
FIG. 12 is a top view of a plenum chamber constituting part of the FIG. 11 vacuum system.

FIG. 11 illustrates schematically a variant of FIGS. 1 and 9 wherein the trays are not moved during inspection, but rather are held motionless while the beam generator 30 is scanned in an X-Y raster by an X-Y motion stage 128. The FIG. 11 vacuum system 130 is similar to the FIG. 9 vacuum system 110, except for the plenum chamber 132 which is necessarily larger as it must serve the entire tray area scanned in X and Y by the beam generator 30. The top wall 133 of the chamber 132 may have a two-dimensional pattern of vacuum openings 134 as shown in FIG. 12.

Figure 14:
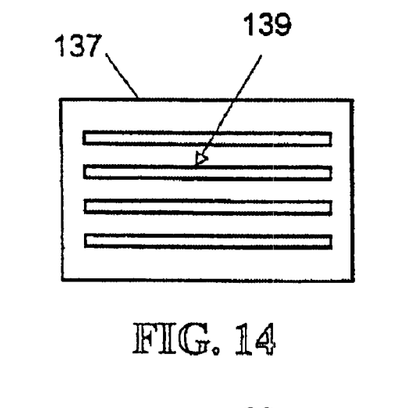

As mentioned briefly and shown schematically, the FIG. 1 drying station 21C has a vacuum dryer 91 to accelerate removal of coupling fluid from the trays 22 and inspected parts. FIG. 13 illustrates a variant of the FIG. 1 system in which a drying station 136 for drying trays 22 includes a plenum chamber 138. The plenum chamber 138 has a top wall 137 with a series of vacuum slots 139 (FIG. 14).

The plenum chamber 138 may be evacuated by its own pump, but in accordance with an aspect of the present invention, it may be coupled through a line 141 to pump 112, pump 112 thus serving as a common pump for parts hold down and for drying the trays and contained parts.

Comparing the perforate top wall 120 of plenum chamber 114 (FIG. 10) with perforate top wall 133 of plenum chamber 138 (FIG. 14), it is evident that the total area of the respective vacuum openings 115 in the hold-down plenum chamber 114 is much less than the total area of the vacuum openings 134 in the dryer plenum chamber 138. That is because the drying station 136 is challenged to dry the entire tray and its contents as quickly as possible, whereas in the hold-down vacuum system 119 the vacuum must be applied only along the scan line of the ultrasonic beam generator 30.

However, in some applications utilizing a common pump as shown at 112 in FIG. 13 may reduce the efficiency of the hold-down vacuum system. The pump will be drawing against the lower pneumatic resistance presented by the dryer plenum chamber and, unless a large pump is utilized, may create a less-than-optimum vacuum level at the hold-down plenum chamber 114.

To overcome the described problem and permit use of a smaller capacity and less costly common pump 112, an allocator valve 140 may be provided (FIG. 15) between lines 116 and 141. In its simplest form the valve 140 may be a simple diverter valve which is controlled by control means 143 to divert the pump head between the hold-down plenum chamber 114 (line 116) and the dryer plenum chamber 138 (line 138). This arrangement would connect the pump 112 exclusively to one chamber or the other at a given time, but not to both at the same time.

Figure 15:
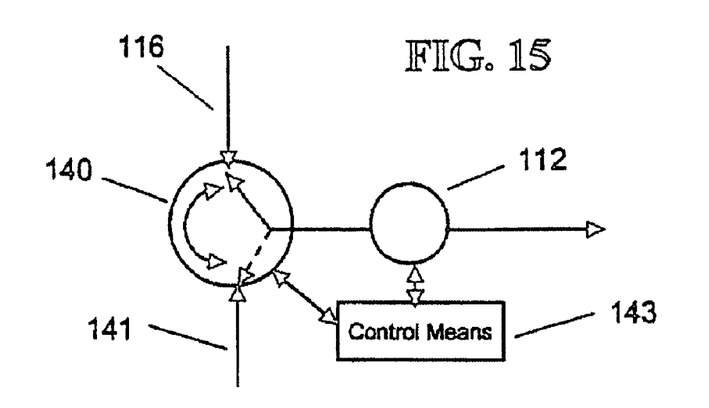

For many applications the allocation valve 140 is configured to allocate a controlled fraction of the output of the pump 112 to the dryer plenum chamber 138 and the hold-down plenum chamber 114. This more flexible approach enables the total vacuum generated, and the fractional outputs allocated to the two uses to be varied in accordance with the type of trays and parts being inspected, desired throughput rate, and other factors.

Figure 16:
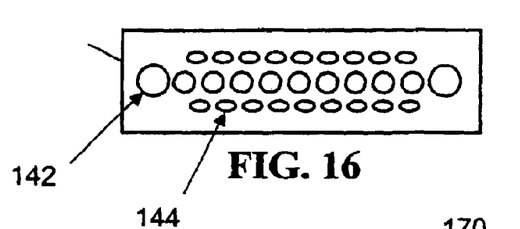
FIGS. 16-17 illustrate variants of the FIGS. 1-15 systems.
Figure 17:
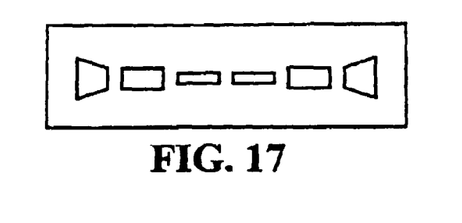

As described above, particularly with respect to FIGS. 9 and 10, the plenum chamber openings 115 are illustrated as having a uniform pattern, shown in FIG. 10 as a single row of apertures of like size and shape. In accordance with an aspect of the present invention, in certain applications it may be desirable to have a non-uniform pattern of openings to compensate for end-of-row conditions, special effects, and so forth. To that end FIG. 16 illustrates a pattern of apertures in top wall 113 of chamber 114 having larger end apertures 142 and additional full or partial rows of apertures 144. Another variant (FIG. 17) illustrates that apertures of different shapes may be employed in the pattern of apertures to define a desired vacuum level profile along the scan axis. The same principle may be employed in the FIGS. 11-12 system wherein the trays are stopped during inspection and the X-Y motion stage 128 moves beam generator 130 in a raster format across the trays.

Each of the embodiments described includes in the hold-down vacuum system the use of a plenum chamber with a pattern of vacuum openings, arrayed either along the X axis, or along both the X and Y axes, to which a vacuum is applied at all times while the beam generator 30 is being scanned. In fact, applying suction to a row-wise pattern of openings may require the use of a larger pump than is necessary. It may be desirable in some applications to have large sized openings to create more suction in the region where the probe is interrogating the parts. However, enlarging all of the holes may counterserve due to excessive losses at the apertures remote from the probe.

However, it is necessary at any given moment during a scan that vacuum be applied only in a localized region (hereinafter termed the "suction region") around the ultrasonic probe and stream of coupling fluid. So long as the localized suction region tracks movement of the beam generator, there is no need to apply suction to openings remote from the location of the probe. In accordance with an aspect of the present invention, to this end a number of arrangements will be described by which a localized suction area is developed which tracks the scanning movement of the beam generator 30.

Figure 18:
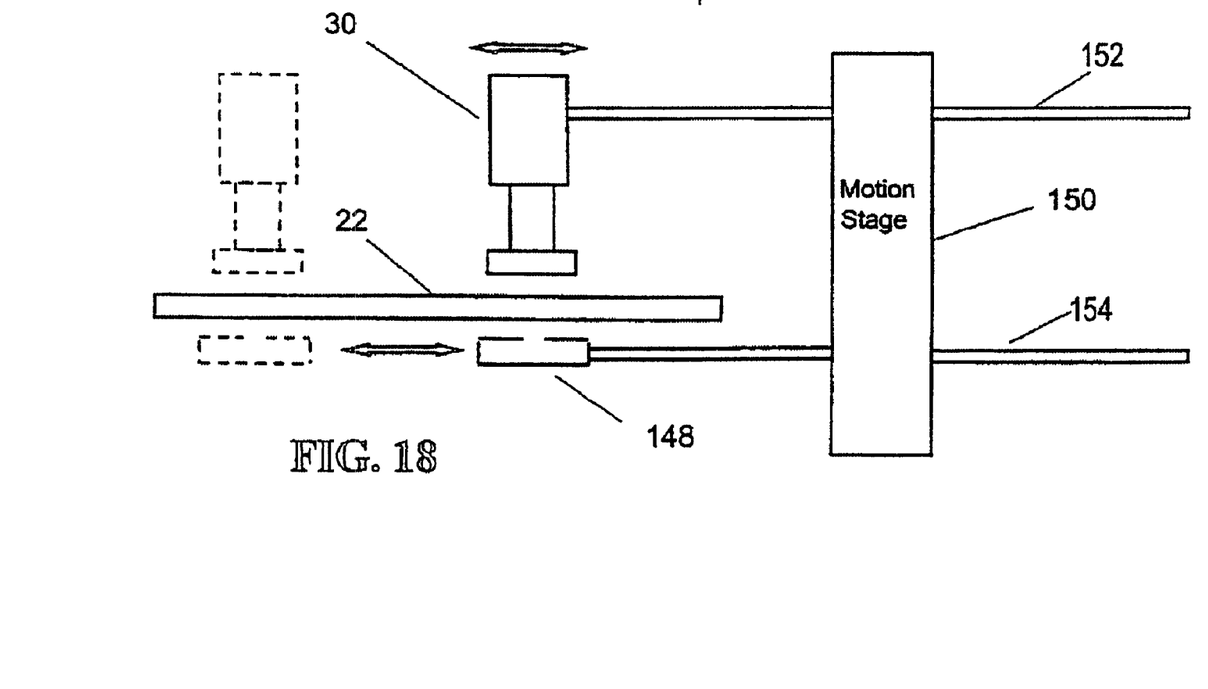
FIGS. 18-19 depict an alternative arrangement wherein a scanning beam generator and a means for developing localized suction in the region of the beam generator are ganged and moved by a common motion stage.

In the FIG. 18 arrangement, the beam generator 30 and a plenum chamber 148 are ganged and moved as one by a motion stage 150, which may move the generator 30 along the X axis, or along both the X and Y axes as described above. The motion stage 150 is shown diagrammatically as being coupled to the beam generator 30 and chamber 148 by connecting members 152, 154. The plenum chamber 148 for the FIG. 18 arrangement is much smaller than the chambers previously described (see FIG. 19), having a pattern of openings 156 sized and configured to develop a suction region effective to immobilize parts being inspected, but not resulting in wasteful suction being applied in areas remote from the probe.

A variant of the FIG. 18 arrangement (not shown) employs separate motion stages for the beam generator 30 and the plenum chamber 148. Common control means (not shown) for the two motion stages synchronizes the movement of generator 30 and chamber 30 so that the localized suction region tracks the movement of the probe.

Figures 19, 20:
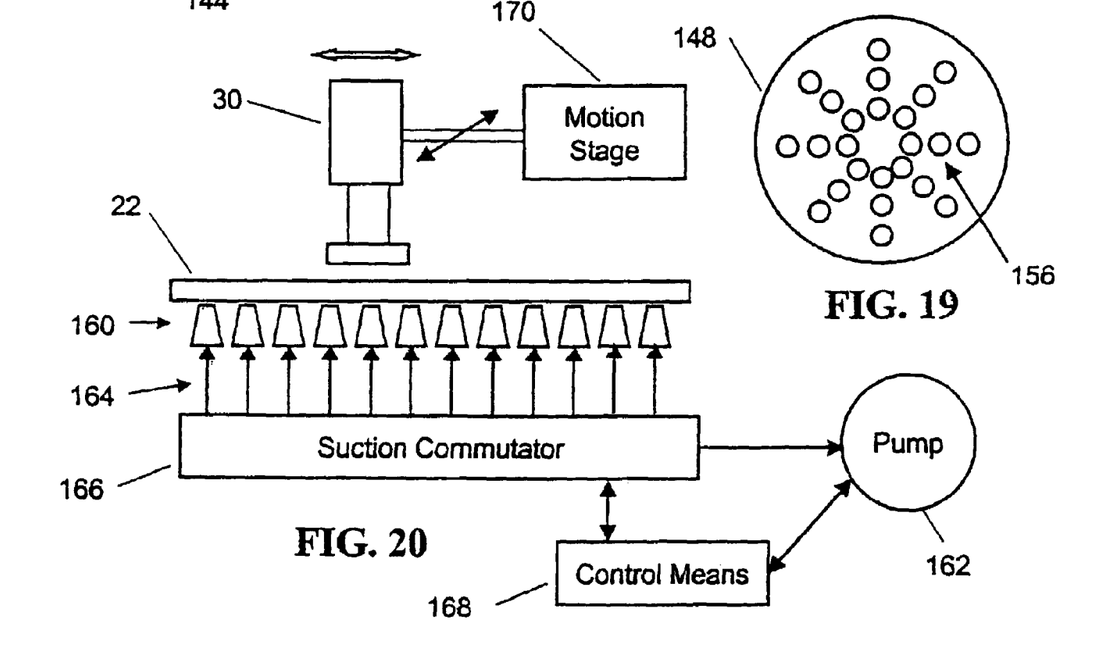
FIG. 20 is another approach for causing a localized suction developing means to track movement of an ultrasonic beam generator.

Yet another variant of the FIG. 18 arrangement is shown schematically in FIG. 20. The advantage of the FIG. 20 arrangement is that it avoids the need for a plenum chamber which must be moved in synchronism with the beam generator 30. In the FIG. 20 arrangement, the tracking means comprises a series of suction elements 160 coupled to a suction pump 162 through a suction distribution system 164 and a suction commutator 166. A control means 168 is coupled to the commutator 166 and pump 162 to cause a fixed or variable head developed in the pump 162 to be selectively applied to the suction elements according to a predetermined program. The suction elements 160 are activated in synchronism with the movement of the beam generator 30 by motion stage 170, and may be activated individually or in groups. The level of suction applied may be uniform or, for reasons given above, be profiled in level along the scan line or raster. The air flow may be modulated, consistent with assuring that any such modulation does not disturb the parts during inspection. In certain applications it may be desirable to modulate the flow of coupling water; the control means would be programmed or otherwise controlled to accommodate such modulation of the coupling water flow.

Among the main benefits of the present invention are improved scanning accuracy as a result of the immobilization of the parts in their respect tray pockets. Effective immobilization of the parts during scanning permits the use of higher scanning rates and therefore a higher inspection throughput rate. An additional benefit of the present invention is that the application of suction to the bottom wall of trays which are distorted tends to flatten them and improve planarity of the scanned parts, particularly if the trays are deformed with a crown.

While particular embodiments of the present invention have been shown and described, it will be obvious to those skilled in the art that changes and modifications may be made without departing from the invention in its broader aspects. For example, the variants and parameter adjustments described with respect to the FIG. 20 system could equally be applied to the other embodiments described herein. Therefore, the appended claims are intended to cover all such changes and modifications as fall within the true spirit and cope of the invention. The matter set forth in the foregoing description and accompanying drawings is offered by way of illustration only and not as a limitation on the scope of the invention.

What is claimed is:

1. A tray-fed scanning acoustic microscope for use with a perforate tray of loosely held parts that is disposed in an insonifying position, the tray-fed scanning acoustic microscope comprising:
   a movable dispenser that is adapted to dispense a flow of coupling fluid through ambient atmosphere and onto a tray of loosely held parts for a period of time when the tray is disposed in the insonifying position;
   wherein the coupling fluid flows though ambient atmosphere in a direction that is generally perpendicular to a plane of the tray, the dispensation of the coupling fluid onto the loosely held parts undesirably tending to agitate them;
   an ultrasonic transducer that is mounted for cooperating movement with the movable dispenser, the ultrasonic transducer also being adapted to direct, when the dispenser is dispensing a flow of coupling fluid onto a tray of loosely held parts, one or more ultrasonic beams through the flow of coupling fluid and onto at least one part that is loosely held in the tray;
   wherein the dispenser and the ultrasonic transducer are movable with respect to and on one side of a tray of loosely held parts that is disposed in an insonifying position; and
   a vacuum system that is adapted to draw a vacuum that is applied for a period of time to a tray of loosely held parts that is disposed in the insonifying position, the vacuum causing air to be draw into the tray to entrain at least some of the flow of coupling fluid that is dispensed onto the parts held in the tray and to thereby create a pressure that at least partially immobilizes the parts on the tray.

2. The tray-fed scanning acoustic microscope of claim 1, wherein the vacuum is applied on the bottom of a tray.

3. The tray-fed scanning acoustic microscope of claim 1, wherein each tray has a perforate bottom wall, and wherein the vacuum system includes a plenum chamber having a wall with vacuum openings addressing said bottom wall of said perforate tray during the scanning operation to draw air into said tray and out through said bottom wall thereof, thereby to at least assist in immobilizing the parts during the scanning operation.

4. The tray-fed scanning acoustic microscope of claim 1, further comprising an X-motion stage coupled to the ultrasonic beam generator.

5. The tray-fed scanning acoustic microscope of claim 4, wherein the vacuum system includes an array of suction apertures aligned with an X axis motion of travel of said beam generator.

6. The tray-fed scanning acoustic microscope of claim 1, further comprising an X-Y-motion stage coupled to the ultrasonic beam generator.

7. The tray-fed scanning acoustic microscope of claim 6, wherein the vacuum system includes an X-Y array of suction apertures aligned with an X-Y axis motion of travel of the beam generator.

8. The tray-fed scanning acoustic microscope of claim 1, wherein the vacuum system includes a diaphragm pump.

9. The tray-fed scanning acoustic microscope of claim 1, wherein the vacuum system recirculates to the coupling fluid dispenser coupling fluid drawn from the trays during scanning.

10. The tray-fed scanning acoustic microscope of claim 1, further including a stationary parts-hold-down structure situated between said ultrasonic beam generator and a tray that is disposed in the insonifying position, the structure conducting coupling fluid from the dispenser to the tray of parts through at least one opening therein which is sized and positioned to also pass the ultrasound beam from the ultrasonic beam generator.

11. The tray-fed scanning acoustic microscope of claim 10, wherein the ultrasonic beam generator is translated transverse to the path of the trays and said opening is a transverse slot of sufficient width in the direction of tray movement to pass coupling fluid and said transversely moved ultrasound beam.

12. The tray-fed scanning acoustic microscope of claim 1, further comprising a drying station for drying trays of parts which have been insonified.

13. The tray-fed scanning acoustic microscope of claim 12, wherein the drying station includes a vacuum dryer for drawing fluid from said trays and parts.

14. The tray-fed scanning acoustic microscope of claim 13, wherein the vacuum dryer and the vacuum system employ a common vacuum pump.

15. The tray-fed scanning acoustic microscope of claim 14, further comprising an allocator valve coupled to the pump and configured to allocate pump head to the dryer and the vacuum system.

16. The tray-fed scanning acoustic microscope of claim 1, wherein the drying station includes a parts dryer, the dryer undesirably tending to dislodge the parts from the trays, and a stationary parts-hold-down device situated closely contiguous to the trays, the hold-down device having a pattern of openings sized and positioned to preclude the parts from being dislodged from the trays by the parts dryer as the trays move past the device.

17. The tray-fed scanning acoustic microscope of claim 1, wherein the vacuum system includes a device that is adapted to develop localized suction in the region of the ultrasonic beam generator.

18. The tray-fed scanning acoustic microscope of claim 1, further comprising a beam motion stage configured to cause the ultrasonic beam generator to scan a the parts that are held in a tray that is disposed in the insonifying position.

19. The tray-fed scanning acoustic microscope of claim 18, further comprising a tracking device that is adapted to cause the localized region of suction to track the movement of the ultrasonic beam generator.

20. The tray-fed scanning acoustic microscope of claim 1, wherein at least one of the parts that are held in the tray comprises a microelectronic sample.

* * * * *